US00PP20107P2

(12) United States Plant Patent
Farrow

(10) Patent No.: US PP20,107 P2
(45) Date of Patent: Jun. 16, 2009

(54) ***ECHINACEA* PLANT NAMED 'CONEKIM'**

(50) Latin Name: *Echinacea purpurea/Echinacea*
Varietal Denomination: Conekim

(75) Inventor: Michael Farrow, Earleville, MD (US)

(73) Assignee: CP Delaware, Inc., Wilmington, DE (US)

( * ) Notice: Subject to any disclaimer, the term of this patent is extended or adjusted under 35 U.S.C. 154(b) by 15 days.

(21) Appl. No.: 12/000,430

(22) Filed: Dec. 12, 2007

(51) Int. Cl.
*A01H 5/00* (2006.01)

(52) U.S. Cl. ..... Plt./428

(58) Field of Classification Search ..... Plt./428
See application file for complete search history.

*Primary Examiner*—Kent L Bell
(74) *Attorney, Agent, or Firm*—Buchanan Ingersoll & Rooney PC

(57) ABSTRACT

A new and distinct highly ornamental *Echinacea* plant is provided. The flowers are attractive and display rose-pink to purple-pink florets. The growth habit is shorter than that of typical *Echinacea purpurea* cultivars, including the 'Kim's Knee High' cultivar (non-patented in the United States). The green foliage contrasts nicely with the colorful flowers. The plant is well suited for providing attractive ornamentation when grown in the landscape or during pot culture.

2 Drawing Sheets

Botanical/commercial classification: *Echinacea purpurea/Echinacea* Plant.
Varietal denomination: cv. Conekim.

SUMMARY OF THE INVENTION

*Echinacea purpurea,* sometimes known as Purple *Echinacea* or Purple Cone Flower, is recognized to be a native American plant found throughout the southeastern portion of the United States. This plant commonly can be grown in most soils in U.S.D.A. Hardiness Zone Nos. 3 to 9, and generally displays high tolerance to heat and drought.

The new *Echinacea* plant of the present invention was discovered during the summer of 2003 at Holly Hill Farms, Earleville, Md., U.S.A., while growing among plants of the 'Kim's Knee High' cultivar (non-patented in the United States). The new cultivar of the present invention is believed to be a whole plant mutation of unknown causation. I was primarily attracted to the single plant of the present invention in view of its shorter growth habit combined with attractive flowers. Had I not discovered and preserved this plant, it would have been lost to mankind.

The new cultivar has been carefully preserved and has been evaluated to confirm that its characteristics are reliably expressed.

It was found that the new *Echinacea* plant of the present invention displays the following combination of characteristics:

(a) forms attractive rose-pink to purple-pink flowers for an extended period of time, (b) displays a shorter growth habit than the 'Kim's Knee High' cultivar (non-patented in the United States), and (c) is well suited for providing attractive ornamentation when grown in the landscape and during pot culture.

When compared to other known *Echinacea purpurea* cultivars, the new cultivar of the present invention can be readily distinguished. Commonly typical cultivars assume a height of approximately 26 to 60 inches; however, a few shorter growing cultivars are known. The 'Kim's Knee High' cultivar commonly assumes a height of approximately 15 to 24 inches and a width of approximately 16 to 24 inches at an age of three years. The 'Robert Bloom' cultivar (U.S. Plant Pat. No. 2,414) commonly reaches a height of 30 to 38 inches and forms dark-red to carmine-purple flowers. The 'Magnus' and 'White Swan' cultivars (both non-patented in the United States) commonly display similar heights. The 'Cygnet White' cultivar (non-patented in the United States) is recognized to display a dwarf growth habit reaching a height of approximately 20 inches and to form white horizontal ray florets. The 'Nana' and 'Rosenelf' cultivars (both non-patented in the United States) also display shorter growth habits, but lack the formation of rose-pink to purple-pink flowers.

The new cultivar of the present invention can be grown to advantage to provide colorful long-lasting ornamentation in the landscape. It also grows well when potted and can be used to brighten patios, as well as other residential settings.

Asexual reproduction of the new cultivar by the use of cuttings has been carried out at West Grove, Pa., U.S.A. Such propagation has confirmed that the unique combination of characteristics of the new cultivar has been stably established and is well transmitted to successive generations. The new cultivar asexually reproduces in a true-to-type manner.

The new cultivar has been named 'Conekim' and is being marketed under the PANTHER PINK trademark.

BRIEF DESCRIPTION OF THE PHOTOGRAPHS

The accompanying photographs show as nearly true as it is reasonably possible to make the same in a color illustration of this character, typical container-grown plants of the new cultivar at West Grove, Pa., U.S.A.

DETAILED DESCRIPTION

Figure 1:
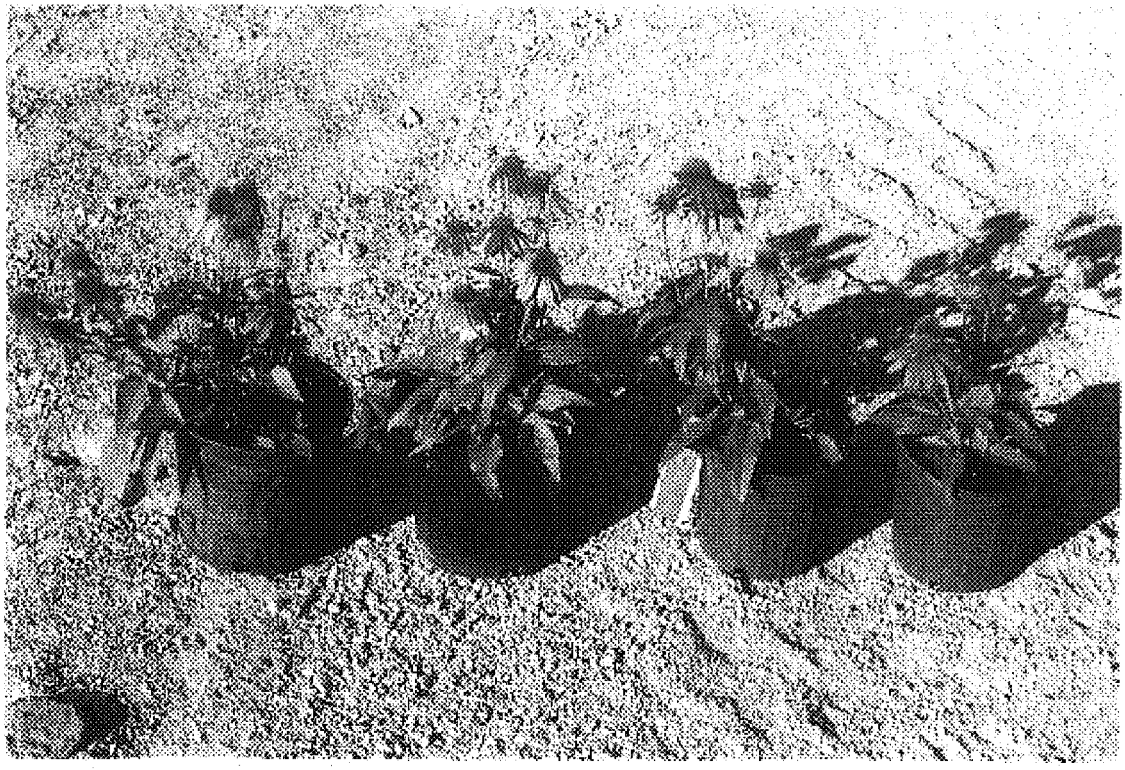
FIG. 1 shows one-year-old flowering plants of the new variety during October 2004, while growing outdoors in one- and three-gallon containers.
Figure 2:
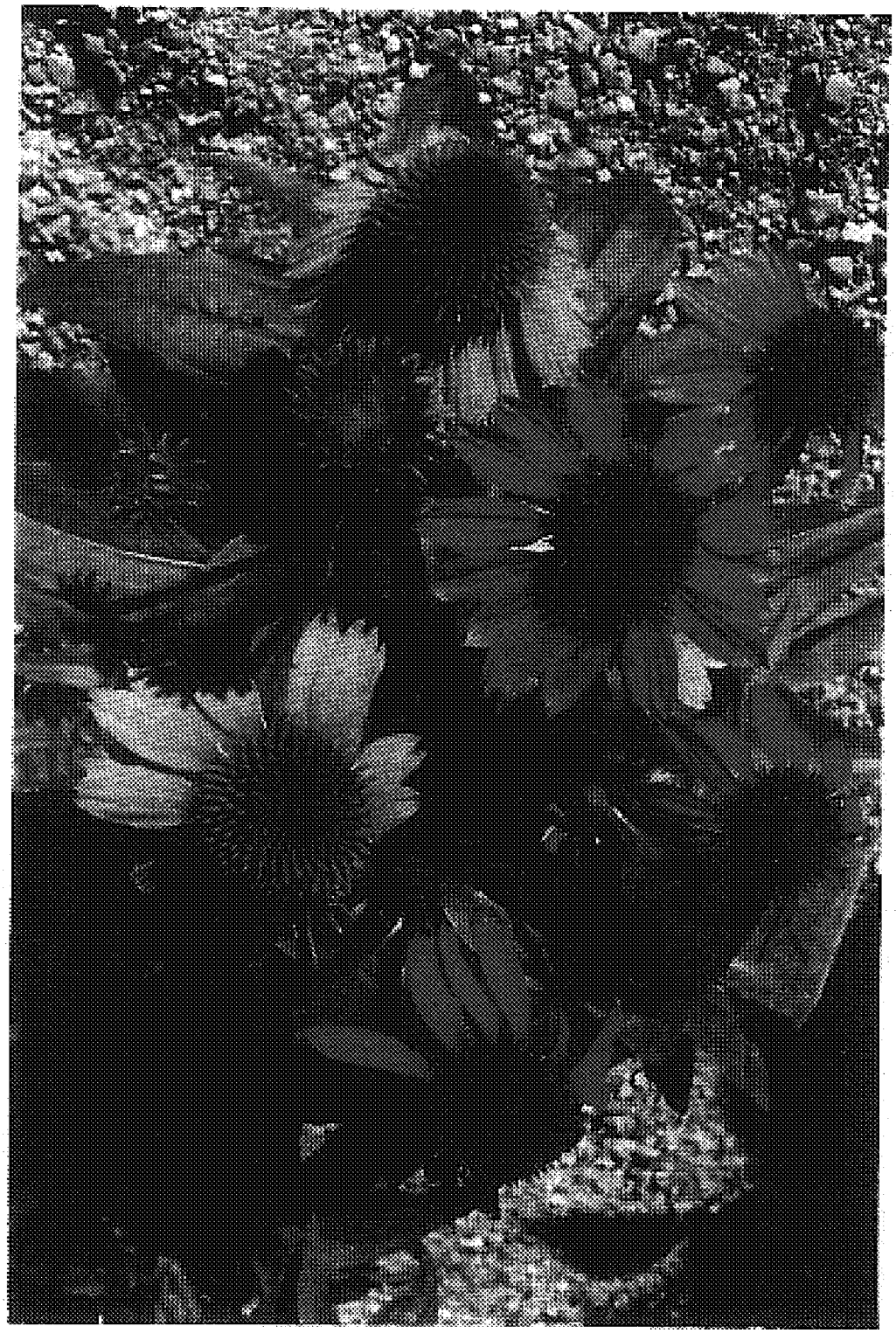
FIG. 2 shows a closer view of the attractive rose-pink and purple-pink flowers as well as the foliage. The photograph was obtained during October 2004 when the plant was approximately one year of age.

The following is a detailed description of the new cultivar of the present invention which was prepared while observing three-year-old plants growing in containers outdoors during September and October at West Grove, Pa., U.S.A. Color terminology is in accordance with the R.H.S. Colour Chart of The Royal Horticultural Society, London, England, except when general color terms are used which are to be accorded their customary dictionary significance.

Type: Herbaceous perennial for ornamental usage.

Plant:

*Growth habit.*—Upright with one to several multiple-branched stems.

*Height.*—Less than that of a typical *Echinacea purpurea* plant. A plant of the new cultivar at an age of 3 years commonly assumes a height of approximately 15 to 18 inches.

*Width.*—Commonly approximately 12 to 24 inches at an age of three years. When grown in the ground, the width tends to be wider than when grown in containers.

*Branching.*—Forms one to several multiple branched stems from a crown or caudex.

*Stem color.*—Light yellow green, near Yellow-Green Group 145B.

*Stem fixture.*—Hispid to hirsute.

*Rooting.*—Fibrous.

Foliage:

*Arrangement.*—Middle cauline in an alternate pattern.

*Shape.*—Lanceolate to lance-ovate, and attenuate or tapered on the petiole.

*Size.*—Commonly approximately 1.5 to 3 inches in width and approximately 1 to 5 times longer in length for basal leaves.

*Frequency.*—Commonly 7 to 8 leaves per stem.

*Margin.*—Mostly toothed particularly on the lower leaves.

*Texture.*—Scabrous on both sides.

*Color.*—Near Yellow-Green Group 147A on the upper surface and near Green Group 138B on the lower surface.

*Petioles.*—Commonly approximately 8 to 15 cm in length, approximately 5 mm in diameter, and display approximately the same color as the peduncles.

Inflorescence:

*Time.*—Commonly initiates flowering during late June, and continues flowering for approximately twelve weeks.

*Buds.*—Nearly round in configuration, approximately 2.5 cm in diameter, and commonly near Yellow-Green Group 151D in coloration.

*Number.*—A typical three-year-old plant may display approximately 45 to 60 flowers at one time and up to approximately 90 flowers per season.

*Lastingness.*—Each flower commonly remains attractive on the plant for approximately 3 to 4 weeks.

*Configuration.*—Solitary heads with up to approximately 24 commonly bifid ray florets which tend to drop with maturity, and approximately 400 disk florets.

*Size.*—Ray florets commonly are approximately 1⅓ to 1¾ inches in length and approximately ¼ to ⅜ inches in width.

*Color.*—Ray florets: upon opening commonly are near Red-Purple Group 58C to Red-Purple Group 64B and commonly are somewhat darker at the center, and with maturity when drooping is underway Red-Purple Group 67A lightening to Red-Purple Group 63D. This compares to an initial coloration near Red-Purple Group 61A for the 'Kim's Knee High' cultivar which lightens to near Red-Purple Group 67C with maturity. Disk florets: upon opening commonly are near Red-Purple Group 59A to Greyed-Purple Group 187C and with maturity changing to dark bronze, near Yellow-Orange Group 23B commonly with golden tips near Greyed-Orange Group 168C.

*Reproductive parts.*—Inconspicuous, and barely visible.

*Fragrance.*—Typical of the species.

*Seeds.*—Appearance is typical of the species, commonly approximately 5 mm in length, approximately 2 mm in width, vary from light to medium tan in coloration, and each flower commonly forms approximately 50 to 125 seeds during observation to date.

*Sepals.*—Each flower commonly includes approximately 24 to 56 small acute sepals, approximately 8 mm in length, approximately 2 mm in width, and of substantially the same coloration as the leaves.

*Peduncles.*—Commonly approximately 12 to 18 inches in length, approximately ¼ inch in diameter, and of the same coloration as the petioles.

Development:

*Hardiness.*—U.S.D.A. Hardiness Zone Nos. 3 to 9.

*Heat tolerance.*—Good.

*Drought tolerance.*—Good.

*Disease resistance.*—No particular susceptibility has been noted during observations to date.

The new cultivar has not been observed to date under all possible environmental conditions. Accordingly, it is possible that the phenotype may vary somewhat with variations in the environment, such as temperature, light intensity, day length, and other cultural conditions without variance of the genotype. For instance, plants of the new cultivar when grown in heavy shade commonly tend to have longer petioles that are of a deeper green coloration. Also, the number of flowers commonly will be reduced under such growing conditions.

I claim:

1. A new and distinct *Echinacea* plant having the following combination of characteristics:

(a) forms attractive rose-pink to purple-pink flowers for an extended period of time, (b) displays a shorter growth habit than the 'Kim's Knee High' cultivar (non-patented in the United States), and (c) is well suited for providing attractive ornamentation when grown in the landscape and during pot culture;

substantially as illustrated and described.

* * * * *